US008986995B2

(12) United States Patent
Turovets et al.

(10) Patent No.: US 8,986,995 B2
(45) Date of Patent: Mar. 24, 2015

(54) METHODS OF DERIVING DIFFERENTIATED CELLS FROM STEM CELLS

(75) Inventors: Nikolay Turovets, Vista, CA (US); Larisa Agapova, Vista, CA (US); Andrey Semechkin, Oceanside, CA (US); Jeffrey Janus, San Diego, CA (US)

(73) Assignee: International Stem Cell Corporation, Oceanside, CA (US)

( * ) Notice: Subject to any disclaimer, the term of this patent is extended or adjusted under 35 U.S.C. 154(b) by 95 days.

(21) Appl. No.: 13/620,082

(22) Filed: Sep. 14, 2012

(65) Prior Publication Data

US 2013/0045534 A1   Feb. 21, 2013

Related U.S. Application Data

(62) Division of application No. 12/629,813, filed on Dec. 2, 2009, now Pat. No. 8,268,621.

(60) Provisional application No. 61/119,570, filed on Dec. 3, 2008.

(51) Int. Cl.
*C12N 5/00* (2006.01)
*C12N 5/02* (2006.01)
*C12N 5/073* (2010.01)

(52) U.S. Cl.
CPC ........ *C12N 5/0603* (2013.01); *C12N 2501/065* (2013.01); *C12N 2501/16* (2013.01); *C12N 2501/415* (2013.01); *C12N 2506/02* (2013.01)
USPC .......................................... 435/377; 435/325

(58) Field of Classification Search
CPC .................... C12N 2501/16; C12N 2501/065; C12N 5/0603; C12N 5/0623; C12N 2501/415; C12N 2506/02
USPC ................................................. 435/477, 325
See application file for complete search history.

(56) References Cited

U.S. PATENT DOCUMENTS

| 2004/0091936 A1 | 5/2004 | West |
| 2005/0170506 A1 | 8/2005 | Sayre et al. |
| 2007/0254359 A1 | 11/2007 | Rezania et al. |

FOREIGN PATENT DOCUMENTS

| JP | 2009225661 A | 10/2009 |
| JP | 5122973 B2 | 1/2013 |
| WO | 2005/063971 A2 | 7/2005 |
| WO | 2006/017134 A2 | 2/2006 |
| WO | 2006/020919 A2 | 2/2006 |
| WO | 2006/071911 A2 | 7/2006 |
| WO | 2007/103282 A2 | 9/2007 |
| WO | 2007/127927 A2 | 11/2007 |
| WO | 2008/124142 A1 | 10/2008 |
| WO | 2009/012428 A2 | 1/2009 |
| WO | 2009/013254 A1 | 1/2009 |
| WO | 2009/018453 | 2/2009 |
| WO | 2009/070592 A2 | 6/2009 |
| WO | 2010/002785 A1 | 1/2010 |

OTHER PUBLICATIONS

Thomson et al. (PNAS, 92:7844-7848 (Aug. 1995).*
NIH (Stem Cells: Scientific Progress and Future Research Directions, Department of Health and Human Services, Chapter 1, pp. 1-4, Jun. 2001).*
Jaenisch et al., Cell, 132: 567-582, 2008.*
Bantscheff et al., "Chemoproteomics Profiling of HDAC Inhibitors Reveals Selective Targeting of HDAC Complexes," *Nature Biotechnol.* (2011), 29(3):255-265, Nature America, Inc.
Brown et al., "Histone Deacetylase Inhibitors Protect Against and Mitigate the Lethality of Total-Body Irradiation in Mice," *Radiat Res.* (2008), 169(4):474-478, Radiation Research Society.
Chen et al., "HDAC Inhibition Promotes Cardiogenesis and the Survival of Embryonic Stem Cells Through Proteasome-Dependent Pathway," *J. Cell. Biochem.* (2011), 112:3246-3255, Wiley Periodicals, Inc.
Cibelli et al., "Parthenogenetic Stem Cells in Nonhuman Primates," *Science* (2002), 295(5556):819.
Harness et al. "Equivalence of Conventionally-Derived and Parthenote-Derived Human Embryonic Stem Cells," *PLoS One* (2011) 6(1):1-9.
Hayashi et al., "Dynamic Equilibrium and Heterogeneity of Mouse Pluripotent Stem Cells with Distinct Functional and Epigenetic States," *Cell Stem Cell* (2008), 3:391-401, Elsevier Inc.
Iascr, "Advancing the Promise: Leading Research Institutions, Patients and Scholars Comment on the Draft NIH Guidelines for Human Stem Cell Research," *Federal Register* (Mar. 11, 2009), 74(46):1-8.
Khan and La Thangue, "HDAC Inhibitors in Cancer Biology: Emerging Mechanisms and Clinical Applications," *Immuno. Cell Biol.* (2012), 90:85-94, Australasian Society for Immunology Inc.
Lin et al., "A Highly Homozygous and Parthenogenetic Human Embryonic Stem Cell Line Derived from a One-Pronuclear Oocyte Following in vitro Fertilization Procedure," *Cell Res.* (2007), 17:999-1007.
Mai et al., "Derivation of Human Embryonic Stem Cell Lines from Parthenogenetic Blastocysts," *Cell Res.* (2007), 17:1008-1019.

(Continued)

*Primary Examiner* — Thaian N Ton
(74) *Attorney, Agent, or Firm* — DLA Piper LLP (US)

(57) ABSTRACT

The present invention provides a method of generating definitive endoderm, mesoderm, or ectoderm cells. The method includes culturing embryonic stem cells, parthenogenetic cells, or induced pluripotent stem cells in the presence of a demethylation agent, a histone deacetylase inhibitor, or a combination thereof, and thereafter, culturing the stem cells in the absence of the agent or combination of agents, to produce definitive endoderm cells, mesoderm, or ectoderm cells.

9 Claims, 4 Drawing Sheets

(56) References Cited

OTHER PUBLICATIONS

Reuter et al., "Epigenetic Changes Induced by Curcumin and Other Natural Compounds," *Genes Nutr.* (2011), 6:93-108, Springer-Verlag.

Revazova et al., "Patient-Specific Stem Cell Lines Derived from Human Parthenogenetic Blastocysts," *Cloning Stem Cells* (2007), 9(3):432-449, Mary Ann Liebert, Inc.

Sun et al., "Histone Deacetylases in Neural Stem Cells and Induced Pluripotent Stem Cells," *J. Biomed. Biotechnol.* (2011), 2011:1-6.

Weinhold, Bob, "Epigenetics," *Environ. Health Perspect.* (2006), 114(3):A160-A167.

D'Amour et al., "Production of pancreatic hormone-expressing endocrine cells from human embryonic stem cells", *Nat Biotechnol.*, 24(11):1392-401 (2006).

Huangfu et al., "Induction of pluripotent stem cells by defined factors is greatly improved by small-molecule compounds", *Nat. Biotechnol.*, 26(7):795-7 (2008).

Li and Ding, "Small molecules that modulate embryonic stem cell fate and somatic cell reprogramming", *Trends Pharmacol. Sci.*, 31(1):36-45 (2010).

McCool et al., "The role of histone acetylation in regulating early gene expression patterns during early embryonic stem cell differentiation", *J. Biol. Chem.*, 282(9):6696-706 (2007).

Supplementary European Search Report (ESR) from EP 09 83 1082, 2013.

Hay et al., "Highly efficient differentiation of hESCs to functional hepatic endoderm requires ActivinA and Wnt3a signaling", Proc. Natl. Acad. Sci. U.S.A., 105(34):12301-12306 (2008). Epub Aug. 21, 2008.

Hori et al., "Growth inhibitors promote differentiation of insulin-producing tissue from embryonic stem cells", Proc. Natl. Acad. Sci. U.S.A., 99(25):16105-16110 (2002). Epub Nov. 19, 2002.

* cited by examiner

| | Pretreatment stage | | Definitive endoderm differentiation stage | | |
|---|---|---|---|---|---|
| trichostatin A | | TSA | | | |
| differentiation signaling | | | Activin A, 100 ng/ml<br>Wnt3a | Activin A, 100 ng/ml | Activin A, 100 ng/ml |
| pluripotency signaling | bFGF<br>Activin A, 20 ng/ml | bFGF<br>Activin A, 20 ng/ml | | | |
| basal medium/ serum | K-DMEM/F12<br>15% KSR | K-DMEM/F12<br>15% KSR | RPMI 1640<br>0% | RPMI 1640<br>0.2% HS | RPMI 1640<br>0.2% HS |
| time | −24 h | 0 h | 24 h | 48 h | 72 h |
| cell stage | pluripotent hpSC | | mesendoderm | | definitive endoderm |
| relative gene expression | OCT4 +++<br>SOX2 +++<br>E-cadherin +++ | | Brachyury +++<br>SOX17 +<br>CER1 + | Brachyury +<br>SOX17 ++<br>CER1 ++<br>CXCR4 ++ | SOX17 +++<br>CER1 +++<br>CXCR4 +++ |

FIG. 1

METHODS OF DERIVING DIFFERENTIATED CELLS FROM STEM CELLS

CROSS-REFERENCE TO RELATED APPLICATIONS

This application is a divisional application of U.S. application Ser. No. 12/629,813 filed Dec. 2, 2009, now issued as U.S. Pat. No. 8,268,621; which claims the benefit under 35 U.S.C. §119(e) to U.S. Application Ser. No. 61/119,570 filed Dec. 3, 2008, now expired. The disclosure of each of the prior applications is considered part of and is incorporated by reference in the disclosure of this application.

BACKGROUND OF THE INVENTION

1. Field of the Invention

The invention relates generally to stem cells, and more specifically to a method for deriving endoderm cells using stem cells.

2. Background Information

During embryonic development, the tissues of the body are formed from three major cell populations: ectoderm, mesoderm and definitive endoderm. These cell populations, also known as primary germ cell layers, are formed through a process known as gastrulation. Following gastrulation, each primary germ cell layer generates a specific set of cell populations and tissues. Mesoderm gives rise to blood cells, endothelial cells, cardiac and skeletal muscle, and adipocytes. Definitive endoderm generates liver, pancreas and lung. Ectoderm gives rise to the nervous system, skin and adrenal tissues.

Human embryonic stem cells (ES) cells are pluripotent cells that can differentiate into a large array of cell types. When injected into immune-deficient mice, embryonic stem cells form differentiated tumors (teratomas). However, embryonic stem cells that are induced in vitro to form embryoid bodies (EBs) provide a source of embryonic stem cell lines that are amenable to differentiation into multiple cell types characteristic of several tissues under certain growth conditions. For example, ES cells become differentiated into neurons in the presence of nerve growth factor and retinoic acid.

Human ES cells and their differentiated progeny are important sources of normal human cells for therapeutic transplantation and for drug testing and development. Required by both of these goals is the provision of sufficient cells that are differentiated into tissue types suitable for a patient's needs or the appropriate pharmacological test. Associated with this is a need for an efficient and reliable method of producing differentiated cells from embryonic stem cells.

Currently, human embryonic stem cells (hES) are derived from three sources: blastocysts remaining after infertility treatments and donated for research, blastocysts generated from donated gametes (oocytes and sperm), and the products of nuclear transfer (NT). Cadaveric fetal tissue is the only source of human embryonic germ cells (hEG). hES and hEG cells offer remarkable scientific and therapeutic possibilities, involving potential for generating more specialized cells or tissues. Ethical concerns about the sources of hES and hEG cells, however, and fears that use of NT for research could lead to use of NT to produce a human being, have fostered a great deal of public discussion and debate.

Parthenogenic activation of mammalian oocytes may be used as an alternative to fertilization by sperm/NT to prepare oocytes for embryonic stem cell generation. Parthenogenic activation is the production of embryonic cells, with or without eventual development into an adult, from a female gamete in the absence of any contribution from a male gamete.

The first human parthenogenetic stem cells (hpSC) were derived from the inner cell mass of blastocysts obtained from unfertilized oocytes activated by chemical stimuli. These cells demonstrated characteristics typical for human embryonic stem cells (hESC), like extensive self-renewal and differentiation in vitro and in vivo into cells of all three germ layers. Human pSC that are histocompatible with significant segments of the human population due to the presence of homozygous HLA genotypes have been derived using an alternate oocyte activation technique (homozygous at all loci) or through the spontaneous activation of an oocyte of rare HLA homozygosity (heterozygous at most loci except HLA). These common HLA haplotype matched hpSC may reduce the risk of immune rejection after transplantation of their differentiated derivatives; thus offering significant advantages for application to cell-based therapies over hESC derived from fertilized oocytes having unique sets of HLA genes. Moreover, creation of hpSC overcomes the ethical hurdles associated with hESCs because the derivation of hpSC originates from unfertilized oocytes.

Two promising applications of pluripotent stem cells involve cell replacement therapy for diabetes or certain liver diseases associated with hepatocyte insufficiency. Production of high purity definitive endoderm (DE) is a critical first step in the generation of therapeutically useful cells of the DE lineage, such as hepatocytes and pancreatic endocrine cells.

Definitive endoderm is formed during gastrulation along with the two other principal germ layers—ectoderm and mesoderm, and during development will give rise to the gastrointestinal and respiratory tracts as well as other organs including the liver and pancreas. The efficient generation of DE from hESC requires two conditions: signaling by transforming growth factor β family members such as Activin A or Nodal as well as release from pluripotent self-renewal signals generated by insulin/insulin-like growth factor signaling via phosphatidylinositol 3-kinase (PI3K). Moreover, adding Wnt3a together with the Activin A increases the efficiency of mesendoderm specification, a bipotential precursor of DE and mesoderm, and improves the synchrony with which the hESCs are initiated down the path toward DE formation.

The developmental capacity of hESC-derived DE has been demonstrated both in vitro and in vivo. Various hESC differentiation protocols utilizing as a first stage differentiation to enriched populations of DE have resulted in production of hepatocyte-like cells exhibiting some characteristics of mature hepatocytes or production of islet endocrine-like cells capable of synthesizing the pancreatic hormones. Transplantation of the hESC-derived DE cells under the kidney capsule of severe combined immunodeficient (SCID) mice resulted in their differentiation into more mature cells of endodermal organs expressing CDX2, villin and hepatocyte-specific antigen. In a mouse model of acute liver injury, the hESC-derived DE further differentiated into hepatocytes was shown to repopulate the damaged liver. Moreover, it was shown that pancreatic endoderm cells differentiated from hESC-derived DE developed in vivo into glucose-responsive endocrine cells that are morphologically and functionally similar to pancreatic islets and protect mice against streptozotocin—induced hyperglycemia.

Numerous studies have contributed to the understanding of global gene expression patterns in pluripotent stem cells and variations therein may partially determine the capacity for differentiation. The control of gene expression is in part regulated by epigenetic mechanisms, including post-translational modifications of histones and DNA methylation. Molecular instruments that disrupt global epigenetic mechanisms may play a role in the elucidation of genetic circuits operating in stem cells. One candidate for global epigenetic modulation is the pharmaceutical agent TSA, a potent histone deacetylase inhibitor. It was shown that TSA treatment of mouse embryonic stem cells causes suppression of important pluripotency factors, including Nanog, a master regulator of stem cell identity, and the activation of differentiation related genes. Interesting, in that study, TSA effect did not support the maintenance or progression of differentiation; upon removal of TSA, the cells reverted to the undifferentiated phenotype.

Provided herein is a method for the differentiation of stem cells to definitive endoderm cells that produces highly enriched cultures of differentiated cells.

SUMMARY OF THE INVENTION

The present invention is based on the seminal discovery that certain conditions are optimal for generating definitive endoderm cells from stem cells.

As such, the present invention provides a method of producing definitive endoderm, mesoderm, ectoderm, or endoderm cells by culturing stem cells in the presence of an agent, wherein the agent alters the epigenetic status of the cell; and thereafter, culturing the stem cells in the absence of the agent, thereby producing definitive endoderm, mesoderm, ectoderm, or endoderm cells. In one aspect, definitive endoderm cells are produced.

In some aspects, the agent that alters the epigenetic status of the cell is a methylation modifying agent and/or an acetylation modifying agent. In particular embodiments, the agent that alters the epigenetic status of the cell is a demethylation agent or a histone deacetylase (HDAC) inhibitor.

In some embodiments the stem cells are embryonic stem cells, parthenogenetic stem cells, somatic stem cells, or induced pluripotent stem (iPS) cells. In certain embodiments, the stem cells are parthenogenetic cells. In one aspect, the parthenogenic cells are cell lines LLC-6p, LLC-12ph, LLC-2p, or LLC-15ph cells. In another embodiment, the stem cells are iPS cells.

In another embodiment, the culturing of the stem cells in the absence of the agent occurs in the presence of Activin A, Wnt3a, or a combination thereof.

In some embodiments, the definitive endoderm cells express one or more markers selected from the group consisting of FoxA2, Sox17, CXCR4, brachyury, and CER1. In certain embodiments, the definitive endoderm cells do not express or express decreased levels as compared to the untreated stem cells of one or more markers selected from the group consisting of E-cadherin and Oct4. In one aspect, the culturing steps are carried out under defined media conditions.

In some embodiments, the definitive endoderm cells are further treated to form cells of the gastrointestinal tract, respiratory tract, or endocrine system. In other embodiments the cells are further treated to form liver or pancreas cells.

In another embodiment of the present invention, there are provided cultures of definitive endoderm cells produced by a method the invention. In one aspect, there are provided cultures of liver cells or pancreatic cells differentiated from endoderm cells produced by the invention methods.

BRIEF DESCRIPTION OF THE DRAWINGS

FIG. 1 shows a schematic of TSA-pretreatment together with differentiation procedures and gene expression for some key markers of definitive endoderm differentiation.

FIG. 3A shows a plot of the effect of TSA-pretreatment on the expression of pluripotency genes OCT4, SOX2 as well as markers of differentiation stage CER1, SOX17, CXCR4 over time. FIG. 3B shows a plot of brachyury (BRACH) expression with and without TSA-pretreatment.

DETAILED DESCRIPTION OF THE INVENTION

Figure 2:
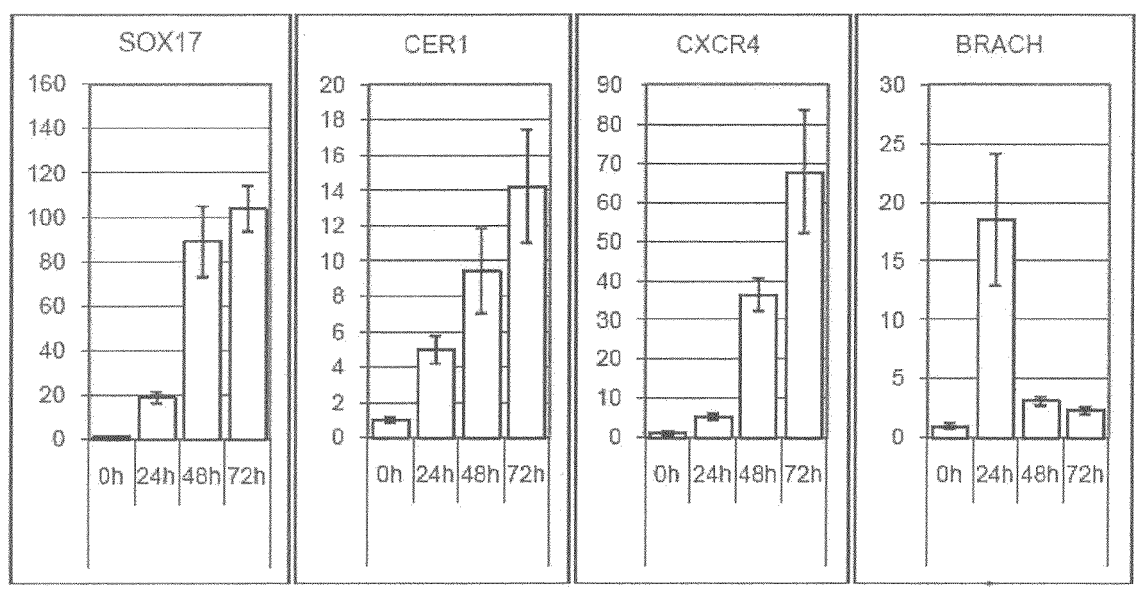
FIG. 2 shows plots of the temporal dynamics of marker gene expression during differentiation of the hpSC into definitive endoderm determined by real-time quantitative PCR. Treatment of the hpSC by Activin A and Wnt3a cause the peak expression of brachyury (BRACH), primitive streak-expressed gene at 24 hours. Expression of SOX17, CER1 and CXCR4 is maximal at 72 hours; 0h, pluripotent hpSC before start of differentiation protocol. Y-axis indicates relative gene expression normalized to the 0h time point.

Before the present composition, methods, and culturing methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure. All publications mentioned herein are incorporated herein by reference in their entirety.

A crucial stage in early human development termed gastrulation occurs 2-3 weeks after fertilization. Gastrulation is extremely significant because it is at this time that the three primary germ layers are first specified and organized. The ectoderm is responsible for the eventual formation of the outer coverings of the body and the entire nervous system whereas the heart, blood, bone, skeletal muscle and other connective tissues are derived from the mesoderm. As used herein, "definitive endoderm" refers to the germ layer that is responsible for formation of the entire gut tube which includes the esophagus, stomach and small and large intestines, and the organs which derive from the gut tube such as the lungs, liver, thymus, parathyroid and thyroid glands, gall bladder and pancreas. A very important distinction should be made between the definitive endoderm and the completely separate lineage of cells termed primitive endoderm. The "primitive endoderm" is primarily responsible for formation of extra-embryonic tissues, mainly the parietal and visceral endoderm portions of the placental yolk sac and the extracellular matrix material of Reichert's membrane.

During gastrulation, the process of definitive endoderm formation begins with a cellular migration event in which mesendoderm cells (cells competent to form mesoderm or endoderm) migrate through a structure called the primitive streak. Definitive endoderm is derived from cells, which migrate through the anterior portion of the streak and through the node (a specialized structure at the anterior-most region of the streak). As migration occurs, definitive endoderm populates first the most anterior gut tube and culminates with the formation of the posterior end of the gut tube.

In vivo analyses of the formation of definitive endoderm, such as the studies in Zebrafish and Xenopus by Conlon et al., 1994; Feldman et al., 1998; Zhou et al., 1993; Aoki et al., 2002; Dougan et al., 2003; Tremblay et al., 2000; Vincent et al., 2003; Alexander et al., 1999; Alexander and Stainier, 1999; Kikuchi et al., 2001; Hudson et al., 1997 and in mouse by Kanai-Azuma et al., 2002 lay a foundation for how one might attempt to approach the development of a specific germ layer cell type in the culture dish using human embryonic stem cells. There are two aspects associated with in vitro ESC culture that pose major obstacles in the attempt to recapitulate development in the culture dish. First, organized germ layer or organ structures are not produced. The majority of germ layer and organ specific genetic markers will be expressed in a heterogeneous fashion in the differentiating hESC culture system. Therefore it is difficult to evaluate formation of a specific tissue or cell type due to this lack of organ specific boundaries. Almost all genes expressed in one cell type within a particular germ layer or tissue type are expressed in other cells of different germ layer or tissue types as well. Without specific boundaries there is considerably less means to assign gene expression specificity with a small sample of 1-3 genes. Therefore one must examine considerably more genes, some of which should be present as well as some that should not be expressed in the particular cell type of the organ or tissue of interest. Second, the timing of gene expression patterns is crucial to movement down a specific developmental pathway.

To further complicate matters, it should be noted that stem cell differentiation in vitro is rather asynchronous, likely considerably more so than in vivo. As such, one group of cells may be expressing genes associated with gastrulation, while another group may be starting final differentiation. Furthermore, manipulation of hESC monolayers or embryoid bodies (EBs) with or without exogenous factor application may result in profound differences with respect to overall gene expression pattern and state of differentiation. For these reasons, the application of exogenous factors must be timed according to gene expression patterns within a heterogeneous cell mixture in order to efficiently move the culture down a specific differentiation pathway. It is also beneficial to consider the morphological association of the cells in the culture vessel. The ability to uniformly influence hESCs when formed into so called embryoid bodies may be less optimal than hESCs grown and differentiated as monolayers and or hESC colonies in the culture vessel.

In view of the desirability of efficient differentiation of pluripotent cells to definitive endoderm cells, some aspects of the present invention relate to in vitro methodology that results in approximately 75-99% conversion of pluripotent cells to definitive endoderm cells. Typically, such methods encompass the application of culture and growth factor conditions in a defined and temporally specified fashion. Further enrichment of the cell population for definitive endoderm cells can be achieved by isolation and/or purification of the definitive endoderm cells from other cells in the population by using a reagent that specifically binds to definitive endoderm cells.

As such, the present invention provides a method of producing definitive endoderm, mesoderm, ectoderm, or endoderm cells by culturing stem cells in the presence of an agent, wherein the agent alters the epigenetic status of the cell; and thereafter, culturing the stem cells in the absence of the agent, thereby producing definitive endoderm, mesoderm, ectoderm, or endoderm cells. In one aspect, definitive endoderm cells are produced.

In some embodiments, the agent that alters the epigenetic status of the cell is a methylation modifying agent and/or an acetylation modifying agent. In particular embodiments, the agent that alters the epigenetic status of the cell is a demethylation agent or a histone deacetylnse (HDAC) inhibitor. The demethylation agent may be a DNA methylatransferase inhibitor, a histone methylation inhibitor and/or histone demethylation inhibitor. In some aspects, the demethylation agent is selected from the group consisting of 5-azacytidine, 5-aza-2'deoxycytidine, 5 fluorocytosine, pseudoisocytosine, Zebularine, Procainamide, polyphenol (−)-epigallocatechin-3-gallate (EGCG), and Psammaplin. In certain aspects, the demethylation agent is 5-aza-2'-deoxycytidine (DAC) or 5-azacytidine. In other embodiments, the acetylation modifying agent is a histone deacetylase (HDAC) inhibitor, a histone acetyltransferase (HAT) inhibitor, histone deacetylase and histone acetyltransferase.

In some embodiments the histone deacetylase (HDAC) inhibitor may be a hydroxamic acid, such as trichostatin A, vorinostat (SAHA), belinostat (PXD101), and LAQ824/LBH589; a cyclic tetrapeptide (such as trapoxin B), a depsipeptides; a benzamide, such as entinostat (MS275), CI994, and mocetinostat (MGCD0103); a electrophilic ketone; an aliphatic acid compound such as phenylbutyrate and valproic acid, isovalerate, valerate, or valproate, nicotinamide, as well derivatives of NAD, dihydrocoumarin, naphthopyranone, and 2-hydroxynaphaldehydes; apicidin, FK228, and sodium butyrate. In one embodiment the HDAC inhibitor is a hydoxamic acid; in one aspect, the HDI is trichostatin A. In another aspect, the HDI is other than sodium butyrate. In some aspects, the histone deacetylase (HDAC) inhibitor is trichostatin A (TSA), sodium butyrate, suberoylanilide hydroxamic acid (SAHA), or N-nitroso-n-methylurea. In other aspects, the histone acetyltransferase (HAT) inhibitor is polyisoprenylated benzophenone (Garcinol) and set/TAF-1 beta. In one aspect, the histone deacetylase inhibitor trichostatin (TSA) is used. In yet another aspect, a combination of 5 aza 2' deoxycytidine and trichostatin (TSA) is utilized.

In one embodiment of the invention, there is provided a method for producing definitive endoderm cells in culture by differentiating stem cells into multipotent definitive endoderm cells in the presence of a pretreatment. As such, in one embodiment, the methods of the invention include culturing stem cells in the presence of an agent, wherein the agent is selected from the group consisting of sodium butyrate, trichostatin A (TSA), a functional equivalent thereof, and a combination thereof, and thereafter, culturing the stem cells in the absence of the agent, to produce definitive endoderm cells.

In some embodiments the stem cells are embryonic stem cells, parthenogenetic stem cells, or induced pluripotent stem (iPS) cells, or somatic stem cells. In some embodiments, hematopoietic stem cells (HSC), adipose-derived stem cells, mesenchymal stem cells (MSC), neural stem cells, endothelial stem cells, neural crest stem cells, or embryonic-like stem cells (ESC) are used. In certain embodiments, the stem cells are parthenogenetic cells. In one aspect, the parthenogenic cells are cell lines LLC-6p, LLC-12ph, LLC-2p, or LLC-15ph cells. In another embodiment, the stem cells are iPS cells.

In another embodiment, the culturing of the stem cells in the absence of the agent occurs in the presence of Activin A, Wnt3a, or a combination thereof.

The stem cells are pretreated with an amount of agent that is sufficient to alter the epigenetic status of the stem cell. The amount of agent required will vary based on the potency of the particular agent. Such amount is readily identified by methods known to the skilled artisan and those provided herein. In one aspect, the pretreatment culturing of the cells in the presence of TSA occurs for about 12-48 hours, and preferably about 24 hours. In another aspect, the culturing in the absence of TSA occurs for about 6-96 hours, or about 6-72 hours, preferably about 24-72 hours. In another embodiment, the TSA is present in a concentration of about 1 nM to 1 µM or about 100 nM to 1 µM. In another embodiment, the culturing steps are carried out under defined media conditions.

In accordance with certain embodiments, the definitive endoderm cells are produced. These cells may be mammalian cells, such as human cells. In some embodiments of the present invention, definitive endoderm cells express or fail to significantly express certain markers. In one non-limiting aspect, one or more markers selected from SOX17, CXCR4, MIXL1, GATA4, HNF3b, GSC, FGF17, VWF, CALCR, FOXQ1, CMKOR1 and CRIP1 are expressed in definitive endoderm cells. In another embodiment, the definitive endoderm cells express FoxA2 and/or Sox17. In another embodiment, one or more markers selected from OCT4, alpha-fetoprotein (AFP), Thrombomodulin (TM), SPARC and SOX7 are not significantly expressed in the definitive endoderm cells. In another embodiment, the definitive endoderm cells do not express E-caherin and/or Oct4.

In some embodiments, the cells are further treated to form cells of the gastrointestinal tract, respiratory tract, or endocrine system. For example, the endodermal cells may be differentiated into cells of the organs of the gastrointestinal system, respiratory tract, or endocrine system. In particular aspects, the cells are further treated to form liver cells or pancreas cells. In some embodiments of the invention, hepatocyte progenitors, that start express AFP (day 7 or day 8 of differentiation) may be used in transplantation.

In other embodiments, mesoderm cells are produced. These cells may be further treated to form any cell derived from a mesoderm lineage. In some embodiments, mesoderm cells may be differentiated by methods known in the art into bone cells, muscle cells, connective tissue, or blood cells.

In other embodiments, ectoderm cells are produced. These cells may be further treated to form any cell derived from a ectoderm lineage. In some embodiments, ectoderm cells may be differentiated by methods known in the art into cells of the nervous system or skin.

In accordance with other embodiments of the present invention, methods of producing definitive endoderm from pluripotent cells are described. In one embodiment, pluripotent cells are derived from a morula. In another embodiment, pluripotent stem cells are stem cells. Stem cells used in these methods can include, but are not limited to, embryonic stem (ES) cells. ES cells can be derived from the embryonic inner cell mass or from the embryonic gonadal ridges. Embryonic stem cells can originate from a variety of animal species including, but not limited to, various mammalian species including humans. In one embodiment, human embryonic stem cells are used to produce definitive endoderm.

The definitive endoderm cell cultures and compositions comprising definitive endoderm cells that are described herein can be produced from pluripotent cells, such as embryonic stem cells. As used herein, "embryonic" refers to a range of developmental stages of an organism beginning with a single zygote and ending with a multicellular structure that no longer comprises pluripotent or totipotent cells other than developed gametic cells. In addition to embryos derived by gamete fusion, the term "embryonic" refers to embryos derived by somatic cell nuclear transfer. A preferred method for deriving definitive endoderm cells utilizes human embryonic stem cells (hESC) as the starting material for definitive endoderm production. The embryonic stem cells used in this method can be cells that originate from the morula, embryonic inner cell mass or those obtained from embryonic gonadal ridges. Human stem cells can be maintained in culture in a pluripotent state without substantial differentiation using methods that are known in the art. Such methods are described, for example, in U.S. Pat. Nos. 5,453,357, 5,670, 372, 5,690,926 5,843,780, 6,200,806 and 6,251,671 the disclosures of which are incorporated herein by reference in their entireties.

The human embryonic stem cells used herein can be maintained in culture either with or without serum. In some embodiments, serum replacement is used. In other embodiments, serum free culture techniques, such as those described in US Patent Application No. 2003/0190748, the disclosure of which is incorporated herein by reference in its entirety, are used.

Stem cells are maintained in culture in a pluripotent state by routine passage until it is desired that they be differentiated into definitive endoderm. In one embodiment, differentiation to definitive endoderm is achieved by providing to the stem cell culture a growth factor of the TGFβ superfamily in an amount sufficient to promote differentiation to definitive endoderm. Growth factors of the TGFβ superfamily which are useful for the production of definitive endoderm are selected from the Nodal/Activin or BMP subgroups. In one embodiment, the growth factor is selected from the group consisting of Nodal, Activin A, Activin B and BMP4. Additionally, the growth factor Wnt3a and other Wnt family members are useful for the production of definitive endoderm cells. In another embodiment, combinations of any of the above-mentioned growth factors can be used.

As used herein, "parthenogenesis" ("parthenogenically activated" and "parthenogenetically activated" is used interchangeably) refers to the process by which activation of the oocyte occurs in the absence of sperm penetration, and refers to the development of an early stage embryo comprising trophectoderm and inner cell mass that is obtained by activation of an oocyte or embryonic cell, e.g., blastomere, comprising DNA of all female origin. As such, a "parthenote" refers to the resulting cell obtained by such activation. Further, a "blastocyst" refers to a cleavage stage of a fertilized or activated oocyte comprising a hollow ball of cells made of outer trophoblast cells and an inner cell mass (ICM). Thus, "blastocyst formation" refers to the process, after oocyte fertilization or activation, where the oocyte is subsequently cultured in media for a time to enable it to develop into a hollow ball of cells made of outer trophoblast cells and ICM (e.g., 5 to 6 days).

As used herein, "activation" refers to a process where a fertilized or unfertilized oocyte, for example, but not limited to, in metaphase II of meiosis, undergoes a process typically including separation of the chromatid pairs; extrusion of the second polar body, resulting in an oocyte having a haploid number of chromosomes, each with one chromatid. Activation includes methods whereby a cell containing DNA of all male or female origin is induced to develop into an embryo that has a discernible inner cell mass and trophectoderm, which is useful for producing pluripotent cells but which is itself is likely to be incapable of developing into a viable offspring. Activation may be carried out, for example, under one of the following conditions: (1) conditions that do not cause second polar body extrusion; (ii) conditions that cause polar body extrusion but where the polar body extrusion is inhibited; or (iii) conditions that inhibit first cell division of the haploid oocyte.

While pathogenesis is not an uncommon form of reproduction in nature, mammals are not known to be capable of this form of reproduction. However, a 10% rate of spontaneous parthenogenesis can be found in oocytes from females of the inbred mouse strain LT/Sv (Ozil and Huneau, Development (2001) 128:917-928; Vrana et al., Proc Natl Acad Sci USA (2003) 100(Suppl 1):11911-11916; Berkowitz and Goldstein, New Eng J Med (1996) 335(23):1740-1748). Oocytes from placental mammals can be induced to undergo parthenogenesis in vitro; however, embryonic development is unsuccessful.

As used herein, "multipotent" or "multipotent cell" refers to a cell type that can give rise to a limited number of other particular cell types. As described above, definitive endoderm cells do not differentiate into tissues produced from ectoderm or mesoderm, but rather, differentiate into the gut tube as well as organs that are derived from the gut tube. In one embodiment, the definitive endoderm cells are derived from hESCs. Such processes can provide the basis for efficient production of human endodermal derived tissues such as pancreas, liver, lung, stomach, intestine and thyroid. For example, production of definitive endoderm may be the first step in differentiation of a stern cell to a functional insulin-producing β-cell. To obtain useful quantities of insulin-producing β-cells, high efficiency of differentiation is desirable for each of the differentiation steps that occur prior to reaching the pancreatic islet/β-cell fate. Since differentiation of stem cells to definitive endoderm cells represents perhaps the earliest step towards the production of functional pancreatic islet/β-cells, high efficiency of differentiation at this step is particularly desirable.

As used herein, a "pluripotent cell" refers to a cell derived from an embryo produced by activation of a cell containing DNA of all female or male origin that can be maintained in vitro for prolonged, theoretically indefinite period of time in an undifferentiated state, that can give rise to different differentiated tissue types, i.e., ectoderm, mesoderm, and endoderm. The pluripotent state of the cells is preferably maintained by culturing inner cell mass or cells derived from the inner cell mass of an embryo produced by androgenetic or gynogenetic methods under appropriate conditions, for example, by culturing on a fibroblast feeder layer or another feeder layer or culture that includes leukemia inhibitory factor (LIF). The pluripotent state of such cultured cells can be confirmed by various methods, e.g., (i) confirming the expression of markers characteristic of pluripotent cells; (ii) production of chimeric animals that contain cells that express the genotype of the pluripotent cells; (iii) injection of cells into animals, e.g., SCID mice, with the production of different differentiated cell types in vivo; and (iv) observation of the differentiation of the cells (e.g., when cultured in the absence of feeder layer or LIF) into embryoid bodies and other differentiated cell types in vitro.

As used herein, "differentiation" refers to a change that occurs in cells to cause those cells to assume certain specialized functions and to lose the ability to change into certain other specialized functional units. Cells capable of differentiation may be any of totipotent, pluripotent or multipotent cells. Differentiation may be partial or complete with respect to mature adult cells.

In order to determine the amount of definitive endoderm cells in a cell culture or cell population, a method of distinguishing this cell type from the other cells in the culture or in the population is desirable. Accordingly, in one embodiment, the methods further relate to cell markers whose presence, absence and/or relative expression levels are specific for definitive endoderm. As used herein, "expression" refers to the production of a material or substance as well as the level or amount of production of a material or substance. Thus, determining the expression of a specific marker refers to detecting either the relative or absolute amount of the marker that is expressed or simply detecting the presence or absence of the marker. As used herein, "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipd, a lipid, a lipoprotein or a small molecule.

For example, in one embodiment, the presence, absence and/or level of expression of a marker is determined by quantitative PCR (Q-PCR). Exemplary genetic markers include, but are not limited to such as FoxA2, Sox17, CXCR4, Oct4, AFP, TM, SPARC, Sox7, MIXL1, GATA4, HNF3b, GSC, FGF17, VWF, CALCR, FOXQ1, CMKOR1, CRIP1, E-cadherin, and other markers, which may be determined by quantitative Q-PCR. In another embodiment, immunohistochemistry is used to detect the proteins expressed by the above-mentioned genes. In another embodiment, Q-PCR and immunohistochemical techniques are both used to identify and determine the amount or relative proportions of such markers.

As such, it is possible to identify definitive endoderm cells, as well as determine the proportion of definitive endoderm cells in a cell culture or cell population. For example, in one embodiment, the definitive endoderm cells or cell populations that are produced express FoxA2 and/or Sox17, but do not express Oct4 and/or E-cadherin.

In another embodiment, the invention provides cell cultures comprising definitive endoderm as well as cell populations enriched in definitive endoderm cells. Thus, in one embodiment, about 50-99%, 60-99%, 70-99%, 75-99%, 80-99%, 85-99%, 90-99% or 95-99% of the cells in culture are definitive endoderm cells. In another embodiment, conversion of a pluripotent cell population, such as a stem cell population, to substantially pure definitive endoderm cell population is contemplated.

As used herein, "defined-medium conditions" refer to environments for culturing cells where the concentration of components therein required for optimal growth are detailed. For example, depending on the use of the cells (e.g., therapeutic applications), removing cells from conditions that contain xenogenic proteins is important; i.e., the culture conditions are animal-free conditions or free of non-human animal proteins.

In some embodiments, the post pretreatment culture conditions include the use of a high level of Activin A for days 1, 2 and 3 of differentiation. Other embodiments include the use of Wnt3a for 1st day of differentiation, after the pretreatment step. In still other embodiments, the culture conditions include the usage FGF4 and BMP2 for days from 4 to 8 of differentiation. In further embodiments, a basal differentiation medium: RPMI 1640 supplemented by Glutamax I and 5% human serum albumin may be used for days from 1 to 8 of differentiation. Still other embodiments include the usage of medium without serum for day 1 of differentiation. In one aspect, low serum medium (0.2% serum) is used for day 2 and 3 of differentiation. In another aspect, 2% serum in differentiation medium is used for days from 4 to 8 of differentiation.

"Differentiated cell" refers to a non-embryonic cell that possesses a particular differentiated, i.e., non-embryonic, state. The three earliest differentiated cell types are endoderm, mesoderm, and ectoderm.

The pluripotent state of the cells used in the present invention can be confirmed by various methods. For example, the cells can be tested for the presence or absence of characteristic ES cell markers. In the case of human ES cells, examples of such markers are identified supra, and include SSEA-4, SSEA-3, TRA-1-60, TRA-1-81 and OCT 4, and are known in the art.

Also, pluripotency can be confirmed by injecting the cells into a suitable animal, e.g., a SCID mouse, and observing the production of differentiated cells and tissues. Still another method of confirming pluripotency is using the subject pluripotent cells to generate chimeric animals and observing the contribution of the introduced cells to different cell types. Methods for producing chimeric animals are well known in the art and are described in U.S. Pat. No. 6,642,433, incorporated by reference herein.

Yet another method of confirming pluripotency is to observe ES cell differentiation into embryoid bodies and other differentiated cell types when cultured under conditions that favor differentiation (e.g., removal of fibroblast feeder layers). This method has been utilized and it has been confirmed that the subject pluripotent cells give rise to embryoid bodies and different differentiated cell types in tissue culture.

The resultant pluripotent cells and cell lines, preferably human pluripotent cells and cell lines, which are derived from DNA of entirely female original, have numerous therapeutic and diagnostic applications. Such pluripotent cells may be used for cell transplantation therapies or gene therapy (if genetically modified) in the treatment of numerous disease conditions.

In this regard, it is known that mouse embryonic stem (ES) cells are capable of differentiating into almost any cell type. Therefore, human pluripotent (ES) cells produced according to the invention should possess similar differentiation capacity. The pluripotent cells according to the invention will be induced to differentiate to obtain the desired cell types according to known methods. For example, human ES cells produced according to the invention may be induced to differentiate into hematopoietic stem cells, muscle cells, cardiac muscle cells, liver cells, islet cells, retinal cells, cartilage cells, epithelial cells, urinary tract cells, etc., by culturing such cells in differentiation medium and under conditions which provide for cell differentiation. Medium and methods which result in the differentiation of ES cells are known in the art as are suitable culturing conditions.

For example, Palacios et al, Proc. Natl. Acad. Sci., USA, 92:7530-7537 (1995) teach the production of hematopoietic stem cells from an embryonic cell line by subjecting stem cells to an induction procedure comprising initially culturing aggregates of such cells in a suspension culture medium lacking retinoic acid followed by culturing in the same medium containing retinoic acid, followed by transferal of cell aggregates to a substrate which provides for cell attachment.

Moreover, Pedersen, J. Reprod. Fertil. Dev., 6:543-552 (1994) is a review article which references numerous articles disclosing methods for in vitro differentiation of embryonic stem cells to produce various differentiated cell types including hematopoietic cells, muscle, cardiac muscle, nerve cells, among others.

Provided herein is a study that demonstrates that the inclusion of TSA-pretreatment of undifferentiated hpSC can improve the efficacy of definitive endoderm (DE) differentiation using a differentiation protocol for hESCs. This pretreatment resulted in an increase in the number of definitive endoderm cells, up to 70% in comparison to a maximum of 45% with non-pretreated hpSC. While not wishing to be bound by any particular theory, it is proposed that inhibition of histone deacetylases caused by TSA-treatment effects a reorganization of the chromatin structure of undifferentiated hpSC, which improves the capacity of undifferentiated cells to respond to the activin A and Wnt3a signals provided in the media. A report in the literature showed that major architectural chromatin proteins are hyperdynamic and bind loosely to chromatin in embryonic stem cells, but upon differentiation, the hyperdynamic proteins become immobilized on chromatin (Meshorer et al., Dev Cell 10(1):105-16, 2006). Karanzali et al (Genome Biol 9(4):R65, 2008) suggested that before full commitment to a differentiated phenotype there might be a window of chromatin 'over-permissiveness' and TSA treatment of undifferentiated ESC might facilitate this transient phase.

One potential outcome of a reorganization in chromatin structure might be an altered capacity for expression of the brachyury gene. In hpSC cultures treated for 24 hours with TSA significantly higher levels of brachyury transcripts were observed. In addition, TSA-treated cultures exhibited a more rapid disappearance of brachyury by day 2 of differentiation. These observations were consistent across all four hpSC lines examined. Previously it was shown that highly enriched definitive endoderm arises from cultures that perform peak-shape expression of brachyury: gene upregulation is changed by downregulation during first 48 hours of Activin A signaling (D'Amour et al, Nat. Biotechnol 23:1534-41, 2005). While not wishing to be bound by any particular theory, we postulate that observed TSA-caused brachyury effect might assist synchronous transition of hpSC through primitive streak intermediate resulted in production of higher portion of definitive endoderm.

Our observations indicate that the cell type generated from hpSC treated by TSA is authentic, definitive endoderm. Marker analysis at the protein and RNA levels is consistent with the formation of DE and excludes the possibility that significant levels of extraembryonic endoderm or other lineages are being produced. Furthermore, DE derived from hpSC first transit through peak of brachyury expression before expressing markers such as CER1, SOX17 and CXCR4. This is reminiscent of the development of DE from a primitive streak intermediate in the vertebrate embryo. Observation that SOX17 expression is initiated in brachyury positive precursors further strengthens the conclusion that the SOX17-positive cells are definitive endoderm rather than primitive endoderm, because brachyury expression has not been identified in the primitive endoderm lineage (Wilkinson D. G. et al., Nature 343:657-9, 1990). As described for the formation of DE from hESC previously, we saw a decline in E-cadherin expression following Activin A treatment, consistent with differentiation being associated with an epithelial to mesenchymal transition similar to that in the primitive streak (D'Amour et al, Nat. Biotechnol 23:1534-41, 2005).

Other reports have described the use of a different histone deacetylase inhibitor, sodium butyrate (NaB), during the production of endoderm cell types from hESCs. In contrast to our protocol the histone deacetylase inhibitor was used in a prolonged fashion simultaneously with the addition of Activin A (Jiang J. et al., Stem Cells 25(8):1940-53, 2007; Hay D. et al., PNAS 105(34):12301-6, 2008; and Hay D. et al., Stem Cells 26(4):894-902, 2008). We find that in similar fashion to TSA, the usage of NaB pretreatment of hpSC also increased the proportion of DE derived from hpSC. However, NaB or TSA applied at the same time with Activin A did not produce any enhancement in the proportion of DE produced from hpSC. Without wishing to be bound by any particular theory, it may be that hpSC and hESCs differ in their basal state chromatin structures and therefore differ in their responsiveness to histone deacetylase inhibitors.

Very little is known about the differentiation capacity of hpSC as all previously published data has only demonstrated their spontaneous differentiation capacity in vitro and in vivo (Revazova et al, Cloning Stem Cells 9(3):432-49, 2007; Revazova et al, Cloning Stem Cells 10(1):11-24, 2008; Lin et al, Cell Research 17:999-1007, 2007; Mai et al, Cell Research 17:1008-1019, 2007). Some reports concerning animal derived parthenogenetic stem cells suggest that parthenogenetic pluripotent stem cells are capable of full-term development, and can differentiate into mature and functional cells of the body. Dopamine neurons generated from primate parthenogenetic stem cells displayed persistent expression of midbrain regional and cell-specific transcription factors, which establish their proper identity and allow for their survival; further, transplantation of these parthenogenetic dopamine neurons restores motor function in hemi-parkinsonian, 6-hydroxy-dopamine-lesoned rats. Moreover, live parthenote pups were produced from in vitro cultured mice parthenogenetic stem cells via tetraploid embryo complementation, which contributed to placenta development.

The data provided herein show that hpSC can respond to signals of direct differentiation at least of DE direction and produce enriched population of the same type differentiated cells. It was found that treatment of undifferentiated hpSC by histone deacetylase inhibitor TSA before application activin A-signaling facilitated derivation DE. This work provides a first step in generation therapeutically useful, histocompatible cells of the definitive endoderm lineage, such hepatocytes and pancreatic endocrine cells from hpSC.

The following examples are intended to illustrate but not limit the invention.

EXAMPLE 1

Production of Definitive Endoderm Cells

The following example demonstrates production of endoderm-like cells derived from LLC-12ph and LLC-6p parthenogenic cell lines. These endoderm-like cells were derived according a protocol of various culture media (D1-Activin A+Wnt3a; D2-Activin A; D3—Activin A; see Tables 1-4, below). However, prior to culture, the parthenogenetic cells were exposed to a pretreatment agent (trichostatin A (TSA)).

TABLE 1

| phSC culture medium |
| --- |
| Knock-out DMEM/F12 |
| 15% KSR |
| 200x NEAA |
| 100x GlutaMAX ™-I |
| 1000x 2-Mercaptoethanol |
| 4 ng/mL bFGF |
| 20 ng/ml Activin A |
| 100x, Penicillin-Streptomycin stock solution |

TABLE 2

| Differentiation medium 1 (D1) |
| --- |
| RPMI 1640 |
| 100x GlutaMAX ™-I |
| 0.5 mg/ml HSA |
| 0.1% Human serum |
| 150 ng/ml Activin A |
| 75 ng/ml Wnt3a |
| 100x, Penicillin-Streptomycin stock solution |

TABLE 3

| Differentiation medium 2 (D2) |
| --- |
| RPMI 1640 |
| 100x GlutaMAX ™-I |
| 0.5 mg/ml HSA |
| 0.5% Human serum |
| 300 ng/ml ITS |
| 150 ng/ml Activin A |
| 100x, Penicillin-Streptomycin stock solution |

TABLE 4

| Differentiation medium 3 (D3) |
| --- |
| RPMI 1640 |
| 100x GlutaMAX ™-I |
| 0.5 mg/ml HSA |
| 0.5% Human serum |
| 300 ng/ml ITS |
| 150 ng/ml Activin A |
| 100x, Penicillin-Streptomycin stock solution |

Accordingly, a protocol for generating definitive endoderm cells is as follows: (i) addition of 100 µM trichostatin A (TSA) to culture medium (phSC culture medium+TSA) and culture cells for about 24 hours; (ii) cultivation of the cells in phSC culture medium+TSA for about 24 hours; (iii) remove TSA from the culture (i.e., cultivation of the cells in culture medium D1 for about 24 hours); (iv) cultivation of the cells in culture medium D2 for about 24 hours; and (v) cultivation of the cells in culture medium D3 for about 24 hours.

Immunostaining showed surface marker expression of FoxA2 (transcription factor) for the parthenogenically derived LLC-6p cells and a lack of the expression for E-cadherin, the marker of undifferentiated cells. Indeed, the overwhelming majority of cells expressed FoxA2.

Immunostaining of a colony of differentiated cells derived from parthenogenetic stem cell line LLC-6p showed expression of Sox17 (transcriptional factor) is one of the markers of definitive endoderm, but not expression of Oct4, a marker of undifferentiated cells. In an exemplary experiment, the majority of cells expressed Sox17, and just single cells expressed Oct4. The Oct4 positive cells remained in a colony like small "cap". Colocalization experiments demonstrated that the majority of cells express either Sox17 or Oct4. As such, cells become either definitive endoderm or do not differentiate, i.e., there were no other types of cells.

EXAMPLE 2

Human Parthenogenetic Stem Cells Produce Enriched Populations of Definitive Endoderm Cells after Trichostatin a Pretreatment The following example illustrates the directed differentiation of human parthenogenetic stem cells (hpSC) to produce enriched populations of definitive endoderm. Moreover, it was found that treatment of undifferentiated hpSC by trichostatin A (TSA) before applying the directed differentiation protocol significantly increased the proportion of definitive endoderm cells in the final population. TSA-pretreated as well as non-TSA-treated hpSC undergoing differentiation toward definitive endoderm demonstrated a similar temporal sequence of gene expression to that which occurs in the course of definitive endoderm differentiation during vertebrate gastrulation and for differentiation of hESCs to definitive endoderm. Generation of the definitive endoderm lineages from hpSC represents a critical first step toward the development of cell-based therapies for liver and pancreas diseases, for example, starting from hpSC.

Cell culture. Undifferentiated hpSC and hESC were maintained on mouse embryo fibroblast feeder layers in KnockOut DMEM/F12 (Invitrogen) supplemented with 15% KnockOut serum replacement (Invitrogen), 0.05 mM nonessential amino acids (NEAA) (Invitrogen), 2 mM Glutamax-I (Invitrogen), penicillin/streptomycin (Invitrogen), 55 µM 2-mercapthoethonol (Invitrogen), 5 ng/ml recombinant human FGF-basic (PeproTech) and 20 ng/ml recombinant human activin A (R&D Systems); for TSA-pretreatment culture medium was supplemented with 100 nM TSA (Sigma) for 24 hours. Cultures were manually passaged at 1:4-1:6 split ratio every 5-7 days. Differentiation was carried out in RPMI 1640 (Invitrogen) supplemented with Glutamax-I, penicillin/streptomycin, 0.5 mg/ml human serum albumin (Sigma), 100 ng/ml recombinant human Activin A, 75 ng/ml recombinant mouse Wnt3a (R&D Systems) for the first 24 hours only. For subsequent days of differentiation media was RPMI 1640 supplemented with 0.2% human AB serum (Fisher BioReagents) and 100 ng/ml recombinant human Activin A. Before initiating differentiation, stem cells were given a brief wash in DPBS (HyClone). FIG. 1 shows a schematic of TSA-pretreatment together with differentiation procedures and gene expression for some key markers of definitive endoderm differentiation. The protocol is divided into two stages: TSA-pretreatment stage (orange color) and DE differentiation stage (green color). TSA-pretreatment is performed against background of the culture conditions that support pluripotency state of the hpSC at time interval from "–24" hours till "0" hours. Differentiation starts from time point "0" hours by applying Activin A- and Wnt3a-signaling and withholding TSA from culture medium. Several markers characteristics of each cell population are listed. The "+" signs demonstrates dynamic of gene expression during differentiation and do not reflect exact quantity of marker's mRNA/protein.

Immunostaining. Cultures were fixed for 20 minutes at room temperature in 4% wt/vol paraformaldehyde in PBS and permeabilized for 40 minutes in 0.1% Triton X-100 in PBS. The following antibodies and dilutions were used: rat anti-Sox17, 1:500 (D'Amour et al, Nat. Biotechnol 23:1534-41, 2005); goat anti-brachyury (AF 2085, R&D Systems), 1:100; rabbit anti Oct-4 (sc-9081, Santa Cruz Biotechnology); mouse anti E-cadherin (13-700, Invitrogen), 1:100; Alexa-488 and Alexa-546 conjugated donkey antibodies against mouse, goat, rat and rabbit (Invitrogen), 1:1000. The slides were mounted in Vectashield mounting media containing DAPI (Vector Laboratories).

Real-time quantitative PCR. Sample collection, reverse transcription and real-time PCR reactions were as previously described (D'Amour et al, Nat. Biotechnol 23:1534-41, 2005).

Flow cytometry. Cells were dissociated using TrypLE (Invitrogen) for 5 minutes then pelleted and resuspended in PBS with 3% FBS (buffer). Labeling was carried out with CXCR4-PE (555976, BD Biosciences) at 10 µl per $1 \times 10^6$ cells for 30 minutes at room temperature. Cells were washed in buffer and resuspended in 1% wt/vol paraformaldehyde. Flow cytometry data were acquired on on a Beckton Dickinson FACS Caliber and analyzed using FACSDiva software (BD Bioscience).

TSA-pretreatment increases the proportion of definitive endoderm. Following on previously described protocols (D'Amour et al, Nat Biotechnol 23:1534-41, 2005; and D'Amour et al, Nat Biotechnol 24:1392-401, 2006), hpSC were differentiated to definitive endoderm (DE) using 3 days treatment with low serum conditions containing Activin A. In addition, Wnt3a was added for the first 24 hours of differentiation in order to synchronize the initiation of hpSC differentiation and enhance mesendoderm specification. Using this approach gene expression associated with vertebrate definitive endoderm including SOX17 and CXCR4 was observed, and expression of CER1 suggests DE of anterior character was generated. (FIG. 2). A transient increase in brachyury expression at 24 hours was observed, indicative of a transition through a mesendoderm intermediate. While after 3 days a portion of the hpSC had differentiated to SOX17-expressing DE, a significant population of cells that maintain expression of the pluripotency marker OCT4 and did not express SOX17 was also observed. After differentiation during 72 hours, SOX17 immunoreactive cells are most numerous in hpSC cultures treated by TSA before applying differentiation conditions. The relative proportion of SOX17+ cells are less than OCT4 immunoreactive cells in non treated hpSC cultures undergone the same differentiation procedure.

FIG. 2 shows plots of the temporal dynamics of marker gene expression during differentiation of the hpSC into definitive endoderm determined by real-time quantitative PCR. Treatment of the hpSC by Activin A and Wnt3a cause the peak expression of brachyury (BRACH), primitive streak-expressed gene at 24 hours. Expression of SOX17, CER1 and CXCR4 is maximal at 72 hours; 0h, pluripotent hpSC before start of differentiation protocol. Y-axis indicates relative gene expression normalized to the 0h time point.

Figure 3A:
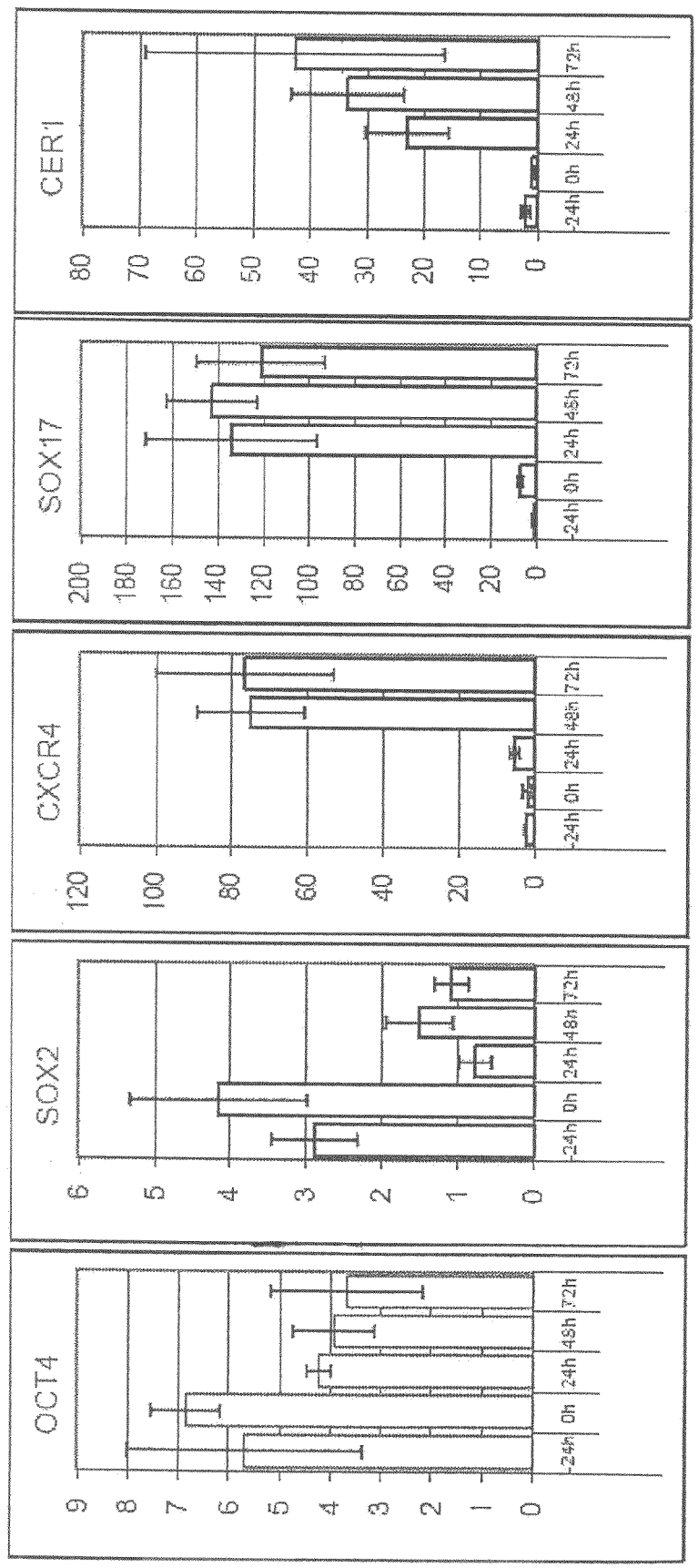
FIGS. 3A and 3B show plots of the temporal dynamics of marker gene expression during differentiation of the TSA-pretreated hpSC into definitive endoderm determined by real-time quantitative PCR.
Figure 3B:
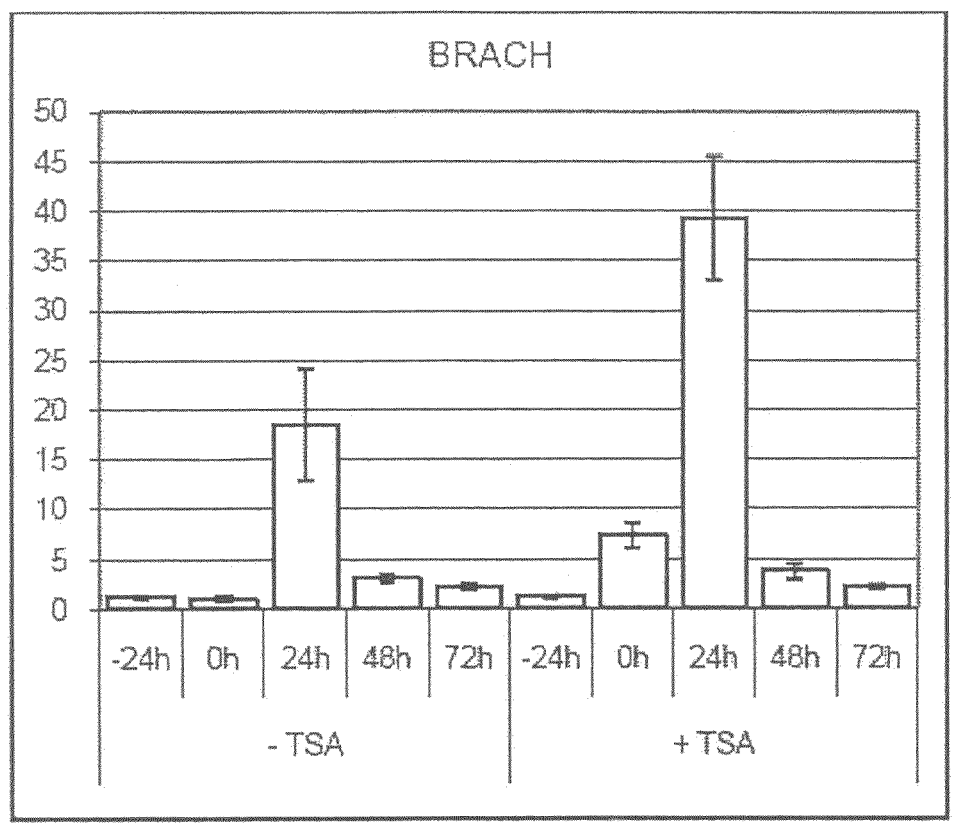

To enhance efficiency of definitive endoderm production and decrease the number of remaining OCT4-positive cells, several different approaches to modulate the capability of hpSC to respond to differentiation stimuli were examined. It was discovered that 24 hours of treatment of hpSC with TSA significantly increased the proportion of SOX17-expressing definitive endoderm. The relative proportion of hpSC-derived definitive endoderm produced with or without TSA-pretreatment is shown at by immunolocalization of SOX17. The proportion of SOX17-positive cells derived from hpSC pretreated with TSA was greater than 70% after 72 hours of differentiation. Moreover, the portion of definitive endoderm cells was quantified by flow cytometry for the cell surface chemokine receptor CXCR4. In contrast to non pretreated hpSC, which always produced less that 45% of CXCR4-positive cells after 3 days of differentiation, TSA-pretreated hpSC demonstrated substantially improved differentiation into definitive endoderm as demonstrated by proportions of CXCR4-positive cells as high as 70%.

hpSC differentiate to definitive endoderm via a primitive streak intermediate. It was observed that TSA pretreatment of undifferentiated hpSC caused some cell death as well as changes in cell morphology. However, there were no significant changes in expression of pluripotency genes OCT4 and SOX2. nor genes associated with DE including CER1, SOX17, and CXCR4 while we did observe a slight upregulation of brachyury expression (FIGS. 3A, 3B). The initiation of overt differentiation by addition of Activin A and Wnt3a stimulated rapid induction of brachyury expression simultaneous with reduced SOX2 and OCT4 gene expression (FIGS. 3A, 3B). Moreover, TSA-pretreated hpSC showed a higher peak level of brachyury gene expression at 24 h and sharper kinetic of reduced expression at 48 h in comparison to non TSA pretreated cultures (FIG. 3B). CER1 and SOX17 transcripts also exhibited a rapid increase in expression during the first 24 hours while the expression of CXCR4 was delayed a further 24 hours and expression of these DE markers was maintained through to day 3 when brachyury was no longer detected (FIG. 3A). It was previously demonstrated that differentiation of hESCs to DE proceeds through a process reminiscent of that occurring during gastrulation in that the hESCs undergo an epithelial-to-mesenchymal transition coincident with initiation of brachyury expression and SOX17-positive cells are derived from brachyury-positive precursors. To trace the origin of the SOX17-expressing cells during hpSC differentiation, SOX17 and brachyury immunoreactivity were characterized over time. At 24 hours there were no SOX17-positive cells but there were a substantial number of brachyury-positive nuclei at the periphery of colonies. However, by 48 hours of differentiation more than half of the cells that expressed SOX17 were also brachyury immunoreactive and at 72 hours the majority of cells expressed SOX17, whereas brachyury protein was no longer detectable. In addition, by 24 hours after the start of differentiation we observed decreased cell-surface immunolocalization of E-cadherin specifically at the periphery of colonies where brachyury-positive cells were observed. In particular, immunofluorescent labeling of differentiating cultures demonstrated coexpression of SOX17 with brachyury (BRACH). There was no detectable immunoreactivity for SOX17 and brachyury after TSA-pretreatment before start of differentiation protocol (0h). Thus, during differentiation of TSA-pretreated hpSC toward definitive endoderm, the dynamics of mesendoderm gene expression and E-cadherin expression and localization was similar to that which occurs during hESC differentiation.

FIG. 3 shows plots of the temporal dynamics of marker gene expression during differentiation of the TSA-pretreated hpSC into definitive endoderm determined by real-time quantitative PCR. FIG. 3A demonstrates that TSA-pretreatment of the hpSC did not cause significant modifications in expression of pluripotency genes OCT4, SOX2 as well as markers of differentiation stage CER1, SOX17, CXCR4 (−24h, before TSA-treatment; 0h, after TSA-pretreatment, before start of differentiation protocol). Application of the differentiation conditions caused SOX2 and OCT4 suppression simultaneously with activation of SOX17, CER1 and CXCR4 expression that attain maximum at 72 hours. (The Y-axis indicates relative gene expression normalized to the 0h time point.) FIG. 3B demonstrates that TSA-pretreated hpSC showed higher level of brachyury (BRACH) expression at 24h and sharper kinetics of disappearance of brachyury's mRNA at 48h (+TSA) in comparison with non TSA-treated cultures (−TSA). (−24h, before TSA-treatment; 0h, after TSA-pretreatment, before start of differentiation protocol. Y-axis indicates relative gene expression normalized to the 0h time point.)

| sample ID | CXCR-4 (CD184) + [% "Intact" Cells] | | | |
|---|---|---|---|---|
| | 3 day | | 4 day | |
| | Ctrl | TSA | Ctrl | TSA |
| 2 p | 34.5 | 61.0 | 42.1 | 58.9 |
| 6 p | 44.5 | 61.2 | 57.7 | 67.6 |
| 8 p | 43.3 | 67.1 | 52.3 | 76.7 |
| 15 ph | 13.9 | 24.1 | 23.7 | 34.2 |

TSA pretreatment improves the efficacy of definitive endoderm production from multiple hpSC lines. The present TSA-pretreatment procedure, together with the described differentiation protocol, was applied to four human parthenogenetic stem cell lines: phESC-1, phESC-3, phESC-5 (Revazova et al., Cloning Stem Cells 9(3):432-49, 2007) and hpSC-Hhom-1 (Revazova et al., Cloning Stem Cells 10(1):11-24, 2008); all data presented thus far were generated using the phESC-3 line. For all 4 lines examined, the use of the TSA-pretreatment procedure increased the number of definitive endoderm cells by 1.4-1.8 fold over non-pretreated cultures as determined by quantification of CXCR4-positive cells using flow cytometry. Moreover, the dynamics of gene expression during differentiation to definitive endoderm from all hpSC lines pretreated with TSA showed that the cells transitioned through the same developmentally appropriate intermediates and express appropriate markers of definitive endoderm.

Although the invention has been described with reference to the above examples, it will be understood that modifications and variations are encompassed within the spirit and scope of the invention. Accordingly, the invention is limited only by the following claims.

What is claimed is:

1. A method of producing definitive endoderm cells comprising:
   a) culturing pluripotent stem cells in the presence of trichostatin A (TSA), with the proviso that activin A is not present; and
   b) thereafter, culturing the pluripotent stem cells in the absence of TSA, and in a media comprising activin A thereby producing definitive endoderm cells.

2. The method of claim 1, wherein the definitive endoderm cells express one or more markers selected from the group consisting of SOX17, CXCR4, MIXL1, GATA4, HNF3b, GSC, FGF17, VWF, CALCR, FOXQ1, CMKOR1, CRIP1 FoxA2, Brachyury, and CER1.

3. The method of claim 1, wherein the definitive endodeitn cells are further treated to form cells of the gastrointestinal tract, respiratory tract, or endocrine system.

4. The method of claim 3, wherein the cells are further treated to form liver or pancreas cells.

5. The method of claim 1, wherein the pluripotent stem cells are embryonic stem cells, parthenogenetic stem cells, or induced pluripotent stem (iPS) cells.

6. The method of claim 1, wherein the culturing of the cells in the presence of TSA occurs for about 12-48 hours.

7. The method of claim 1, wherein the culturing in the absence of TSA occurs for about 6-96 hours, or about 6-72 hours, preferably about 24-72 hours.

8. The method of claim 1, wherein the TSA is present in a concentration of about 1 nM to 1 μM.

9. The method of claim 1, wherein the cells are mammalian cells.

* * * * *